United States Patent [19]

Halpern et al.

[11] Patent Number: 4,874,901
[45] Date of Patent: Oct. 17, 1989

[54] PROCESS FOR THE PRODUCTION OF POLYFLUORINATED ETHERS

[75] Inventors: Donald F. Halpern, Fanwood; Mark L. Robin, South Plainfield, both of N.J.

[73] Assignee: BOC, Inc., New Providence, N.J.

[21] Appl. No.: 191,442

[22] Filed: May 6, 1988

[51] Int. Cl.$^4$ .............................................. C07C 41/22
[52] U.S. Cl. ..................................................... 568/683
[58] Field of Search ........................................ 568/683

[56] References Cited

U.S. PATENT DOCUMENTS 3,683,092  8/1972  Regan et al. ...................... 568/683
3,862,241  1/1975  Terrell ................................. 568/683
4,762,856  8/1988  Terrell ................................. 514/722

OTHER PUBLICATIONS

Mason et al, J.A.C.S. 78, 1682–1684, 1956.

Primary Examiner—Howard T. Mars
Attorney, Agent, or Firm—R. Hain Swope; Larry R. Cassett

[57] ABSTRACT

Sodium or potassium fluoride has been found to efficiently fluorinate the chloro atom adjacent the ether oxygen in chloro-fluoro organic ethers. The reaction proceeds efficiently without added solvent at an elevated temperature and pressure.

12 Claims, No Drawings

PROCESS FOR THE PRODUCTION OF POLYFLUORINATED ETHERS

BACKGROUND OF THE INVENTION

This invention relates to a process for fluorinating halogenated ether compounds, more particularly the replacement of one or more chloro atoms alpha to an ether oxygen by a fluoro atom. This process is especially useful for the synthesis of valuable inhalation anesthetics.

Although the most direct route to the preparation of fluorine containing organic compounds may be the replacement of hydrogen in an organic compound, such a reaction is problematic. It is well known that the reaction of elemental fluorine with organic compounds to replace hydrogen with fluorine is problematic. Partially fluorinating organic compounds, so as to have fluorine atoms in the desired positions, is usually not possible in satisfactory yields. Although certain halogens other than fluorine, e.g. chlorine and bromine, generally react well with a wide variety of organic compounds under moderate conditions to give high yields, the reaction of fluorine is usually violent and accompanied by the formation of undesirable and unrecyclable side products.

Besides elemental fluorine, other agents have been tried to selectively replace hydrogen with fluorine. Among the fluorinating agents tried have been hydrogen fluoride, cobalt trifluoride, silver difluoride, etc. However, little success has been reported in attempting to selectively replace hydrogen with fluorine.

For the above reasons, it is generally preferable to first prepare a corresponding chloro compound and then replace the chloro atom with a fluoro atom. Metal fluorides have heretofore been proposed in general to replace chlorine with fluorine in organic compounds. For example, British patent specification 727,768 discloses the preparation of fluoroesters, ethers, and acetals with potassium fluoride in the presence of a solvent containing acetamide and/or N-methyl acetamide.

In *Tetrahedron Lett*, 27(13), 1499–500 (1986), Escoula et al. disclose a fluoride-chloride exhange reaction employing potassium fluoride, catalyzed by ammonium salts in the presence of formamide in place of water. Monochlorooctane is an exemplary starting material.

Mason et al, in *J. Amer. Chem. Soc.*, 78, 1682 (1956) disclose preparing compounds of the type $CCl_3CHFOR$ by employing metal fluorides for the exhange reaction with $CCl_3CHClOR$. To improve the yield of the fluoroether, Mason et al. teaches dropping the chlorinated ether into potassium fluoride in Nujol TM at 140°. However, even under these conditions, polymerization occurred with the use of potassium fluoride. Mercuric fluoride was the preferred reagent.

In *Chemistry of Organic Fluorine Compounds*, John Wiley & Sons, New York (1976), M. Hudlicky states, that for the replacement of non-activated halogen atoms by fluorine, traditionally potassium fluoride was avoided, and that only recently has it been applied to the replacement of poorly reactive halogen atoms. The conventional solution to this problem has been the application of a suitable solvent. Hudlicky further states that whereas the yields of the reaction of aliphatic halogen derivatives with potassium fluoride without solvent rarely exceed 20–30%, the use of solvents can significantly raise yields. Hudlicky also states that in order to obtain maximum yields, pure and absolutely dry chemicals must be used, and that the reaction is best carried out by heating one mole of the halogen derivative with a 100% excess of potassium fluoride and 700 g of diethylene glycol at a temperature of 125±5° C. with vigorous stirring. Hudlicky further states that compared to potassium fluoride the extent of applications for sodium fluoride is very narrow.

The *Kirk-Othmer Encyclopedia of Chemical Technology* (1980) states that potassium chloride by-products from reactions with organic chlorides deposit on the potassium fluoride crystal surfaces, significantly retarding the reactions. Polar solvents such as dimethyl sulfoxide or formamides, and rapid stirring are useful in overcoming this drawback.

The need for new and improved procedures for the preparation of certain classes of fluorine containing organic compounds is evident.

It is therefore an object of the present invention to provide a method for the preparation of fluorine containing organic compounds. Still a further object is to provide a method whereby a fluorine containing organic compound may be prepared from a partially chlorinated, brominated or iodinated organic compound. An additional object is to provide a method for preparing a fluorine containing organic compound whereby the formation of undesirable decomposition or side products is substantially avoided. An additional object is to provide a fluorination method which is not subject to certain of the disadvantages set forth above.

It is a further object of the present invention to provide a new and improved process for the production of fluoro or fluoro-chloro substituted organic ether compounds. A further object is the provision of a new and improved method of fluorinating such compounds by means of alkali metal fluorides, and more particularly by means of sodium or potassium fluoride.

Other objects will become apparent from the following specification and claims.

DETAILED DESCRIPTION OF THE INVENTION

According to the present invention, the foregoing and related objects are accomplished readily and economically by contacting sodium fluoride or potassium fluoride with a compound having the generic structure shown below:

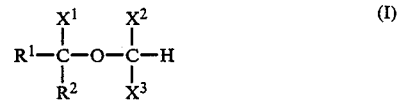

wherein $X^1$, $X^2$ and $X^3$ are H, Cl, or F with the proviso that at least one is chloro and $R_1$ and $R_2$ are either hydrogen or halo lower alkyl with the proviso that at least one is halo lower alkyl.

The reaction of the present invention therefore is applicable, to the chloro in the carbon alpha to the ether oxygen in halogenated lower alkoxy groups. By lower alkyl is meant alkyl groups of 1 or 2 carbon atoms. Preferably halo lower alkyl is trifluoromethyl.

The process of the present invention is inexpensive and efficient and produces the fluoro derivative of compounds of formula I above in excellent yield. Examples of fluorine containing organic compounds which may be prepared according to the method of the invention include inhalation anesthetics such as sevoflurane.

Sodium fluoride or potassium fluoride are inexpensive solid materials which are commercially available. Sodium fluoride or potassium fluoride in granulated or coursely powdered form may be suitably employed. In the present invention, drying or activation of the materials is not necessary.

The reaction vessel, which may be of iron, nickel or of other material resistant to the reactants and reaction products under the conditions of flourination is maintained at the desired reaction temperature by any convenient means. Heating may be effected in any of a number of ways, such as by electrical resistance heaters, by carefully controlled gas flames, or by immersing the reaction vessel in a suitable high-boiling liquid.

The organic reactant is preferably introduced into the reaction vessel in the form of a liquid. The organic reactant and alkali metal salt may be mixed together in any convenient way, e.g., the organic reactant may simply be stirred in a vessel at the desired temperature and the alkali metal salt added gradually thereto. The fluorination reaction is carried out without added solvent, eliminating the problem of spent solvent disposal.

The reactants need not be stirred and a stoichiometric excess of the alkali fluoride need not be employed. The molar ratio of alkali metal salt to organic reactant is suitably 0.3:1 to 3:1. A ratio of about 1:1 (a slight excess of alkali metal salt) is preferred.

Fluorination of a hydrogen and halogen containing organic substance using an alkali metal fluoride as the active fluorinating agent is usually carried out at a temperature between about 100° and about 300° C. and preferably between about 150° and about 250° C. Temperatures sufficiently high to cause the formation of substantial amounts of undesired by-products should be avoided.

Flourination is carried out at an elevated pressure, suitably 15 to 1100 psig and preferably 40 to 600 psig.

Either batch or continuous operation is suitable. In order to effect the satisfactory completion of fluorination of the organic reactant in a continuous process, it may be necessary to limit the rate of reactant passing through the reaction vessel. For this reason, it may be preferable to recycle the organic reactant. By a suitable arrangement of reaction vessels and auxillary apparatus such as distillation towers, the process can be carried out efficiently.

The reaction product may be treated in a conventional manner to recover the desired product in pure form. Since no added solvent is employed, the separation is greatly facilitated. The liquid may be fractionally distilled and the desired product collected. Any unreacted starting material may, if desired be recycled to the fluorination reaction vessel. Other ways of recovering the desired product from the reaction mixture will be apparent to those familiar with the art and the present invention is not limited to such methods of recovery. For example, the reaction mixture may be decanted or otherwise treated to separate the organic and inorganic portions thereof.

In all cases, following reaction, carbonaceous materials are found in the reactor and the initially white alkali metal solids take on a brownish color, an effect more pronounced with potassium fluoride. For additional product, treatment of the brown solids remaining in the reactor with ice water yields an emulsion which upon distillation affords the reaction product.

The following examples are provided by way of illustration only and are not to be construed as limiting.

Gas chromatograph (GC) analyses were performed on a GOW-MAC Model HP5790 having a thermal conductivity detector and HP 3392A integrator. The column was 1% SP1000 on 60/80 Carbopack B, $\frac{1}{8}''$ diameter$\times$20'. A TCD (thermal conductivity detector) temperature of 214° C., an injector temperature of 182° C., a column temperature of 190° C., and a flow rate of 60 cc/min were set. All GC results are reported in area %.

As previously mentioned, all reagents are readily available from commercial sources and unless otherwise noted may be used as received.

The following definitions are employed:

$$\% \text{ conversion} = \frac{\text{moles products}}{\text{moles starting material fed}} \times 100$$

$$\% \text{ yield} = \frac{\text{moles product}}{\text{moles starting material consumed}} \times 100$$

$GC$ = gas chromatograph
$t_r$ = GC retention time (minutes) from injection point

EXAMPLE 1

Reaction of isoflurane with KF at elevated temperature and pressure.

A 1 liter autoclave (316SS, Parr) was charged with 171 g (0.93 moles) isoflurane and 116 g (2.0 moles) potassium fluoride. The reaction mass was heated with stirring to 278° C. After 18 hours at 278° C., the pressure was 500 psi. The autoclave was then cooled to room temperature for transfer to the laboratory. Products were then distilled into a dry ice cooled trap by heating the autoclave on a hot plate. The trap contents (134 g) were distilled through a four foot vacuum jacketed column packed with glass beads to give 20.8 g $CHF_2OCHFCF_3$ (bp 23.5° C.). The material remaining in the distillation flask (104.0 g) was 98% isoflurane. Based on the materials isolated, the percent conversion was 13% (33% yield). Details of the distillation are given below.

| Fraction | Weight | Head T (°C.) | Reflux Ratio | Purity* |
|---|---|---|---|---|
| 1 | 1.6 | 18–23 | 100:1 | 90.0 |
| 2 | 2.4 | 23 | 100:1 | 93.5 |
| 3 | 1.5 | 23 | 100:1 | 95.7 |
| 4 | 0.9 | 23 | 100:1 | 97.0 |
| 5 | 16.1 | 23–33 | 100:1 | 92.9 |

*gc, area % $CHF_2OCHFCF_3$

The structure of $CF_3CHFOCF_2H$ may be confirmed by the following instrumental data:

$^1H$ NMR: doublet of quartets at $\delta$ = 5.9 ppm,
$J_{OCHF}$ = 54.3 Hz
$J_{CHF-CF_3}$ = 2.8 Hz
triplet at $\delta$ = +6.5 ppm, $J_{CF_2H}$ = 70.4 Hz
$^{19}F$ NMR: $\phi_{CF_2H}$ = $-86.1$ ppm
$\phi_{CHF}$ = $-146.5$ ppm
$\phi_{CF_3}$ = $-84.5$ ppm
$^4J_{F-F(CH_2HOCHF)}$ = 5.8 Hz
$J_{F-F(CF_2)}$ = 160.3 Hz
$J_{F-H(CF_2H)}$ = 70.0 Hz
$J_{F-H(CHF)}$ = 55.3 Hz
Mass Spectrum (electron impact):
Format: m/e (intensity), fragment id
149(1)$C_3H_2F_5O$, M-F; 101(17)$C_2HF_4$; 69(9)$CF_3$;
51(100)$CF_2H$; 32(9)$CHF$; 31(18)$CF$

EXAMPLE 2

Reaction of isoflurane with NaF at elevated temperature and pressure.

A 1 liter autoclave (316SS, Parr) was charged with 399 g (2.2 moles) isoflurane and 84 g (2.0 moles) of sodium fluoride. The reaction mass was heated to 283° C. without stirring. After 24 hours at 283° C., the pressure was 1160 psi. The autoclave was then cooled to ca. 10° C. and the crude products (228 g) transferred by pouring into a distillation flask. Distillation through a four foot vacuum jacketed column packed with glass beads gave 73.4 g $CHF_2OCHFCF_3$. The material remaining in the distillation flask was found by GC analysis to be 99.6% isoflurane. Based on the materials isolated the percent conversion was 20% (31% yield). Details of the distillation are given below.

| Fraction | Weight | Head T (°C.) | Reflux Ratio | Purity* |
|---|---|---|---|---|
| 1 | 2.4 | 18 | 100:1 | 74.2 |
| 2 | 27.0 | 18–22 | 100:1 | 92.1 |
| 3 | 7.1 | 22 | 100:1 | 97.3 |
| 4 | 28.7 | 22 | 100:1 | 98.3 |
| 5 | 12.6 | 22–30 | 100:1 | 92.2 |

*gc, area % $CHF_2OCHFCF_3$

EXAMPLE 3

Preparation of $CHF_2OCHFCF_3$

Isoflurane (171 g) was combined with 116 g of potassium fluoride in the absence of solvent and the resulting mixture was heated in an autoclave at 28° C. at 500 psi for 18 hours and then allowed to cool. The cooled mixture was subjected to gas chromatography which showed the presence of 68% of the compound $CHF_2OCHFCF_3$ and 30% unreacted isoflurane. Treatment of this mixture with excess bromine trifluoride at 15° C. in a glass vessel followed by washing with dilute sodium hydroxide and drying yielded 50 g of 98% pure product (30% yield).

EXAMPLE 4

Conversion of $(CF_3)_2CHOCHCl_2$ to $(CF_3)_2CHOCHF_2$

In a 100 ml Parr reactor, 4.6 g of NaF and 12.6 g of $(CF_3)_2CHOCHCl_2$ were combined without stirring. The reactor was heated to about 190° C. and an exotherm carried the temperature to 219° C. Maintaining the temperature, the original pressure of 169 psi was increased to 190 psi. After 17 hours, the reactor was cooled to room temperature. The GC showed 87% conversion to $(CF_3)_2CHOCHF_2$.

EXAMPLE 5

Preparation of $(CF_3)_2CHOCH_2F$ (Sevoflurane)

A 1 liter stainless steel autoclave (Parr) was charged with 127.3 g (2.19 mole) of potassium fluoride and 434.6 g (2.01 mole) of $(CF_3)_2CHOCH_2Cl$. The autoclave was then sealed and the reaction mass heated at 185° C. for 19 hours, during which time a pressure of 280 psi developed. The reactor was then cooled, the contents treated with water and the organic material distilled to afford 241 g (1.21 mole) of $(CF_3)_2CHOCH_2F$ and 80 g (0.4 mole) of $(CF_3)_2CHOCH_2Cl$, corresponding to a 60% conversion (75% yield). The structure of $(CF_3)_2CHOCH_2F$ (Sevoflurane), b.p. 56° C., may be confirmed by the following instrumental data:

| | |
|---|---|
| $^1$H NMR: | septet at $\delta = +4.4$ ppm, $J_{H-CF_3} = 5.9$ Hz |
| | doublet at $\delta = +5.4$ ppm, $J_{CH_2F} = 53.5$ Hz |
| $^{19}$F NMR: | triplet, $\phi = -74.6$ ppm, $J_{CH_2F} = 53.5$ Hz |
| | doublet, $\phi = -155.1$ ppm, $J_{HCF_3} = 5.9$ Hz |
| Mass Spectrum (electron impact): | |
| Format: m/e (intensity), fragment id | |
| 199(1), $C_4H_2F_7O$, M-H; 181(11),$C_4H_3F_6O$, M-F; | |
| 151(5),$C_3HF_6$, $(CF_3)_2CH$; 131(53), $C_3F_5$; 79(20), | |
| $C_2HF_2O$; 69(33),$CF_3$; 51(20),$CF_2H$; 33(100),$CH_2F$ | |

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

What is claimed:

1. A method for the fluorination of a compound of the formula:

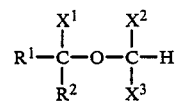

wherein $X^1$, $X^2$ and $X^3$ are hydrogen, chloro, or fluoro, with the proviso that at least one is chloro and $R^1$ and $R^2$ are either hydrogen or halo lower alkyl with the proviso that at least one is halo lower alkyl, said method comprising reacting sodium fluoride or potassium fluoride with said compound at an elevated temperature and pressure in the absence of added solvent.

2. A method according to claim 1, wherein $R^1$ and $R^2$ are either hydrogen or trifluoromethyl with the proviso that at least one is trifluoromethyl.

3. A method according to claim 1, wherein said compound is isoflurane.

4. A method according to claim 1, wherein said compound is $(CF_3)_2CHOCHCl_2$ or $(CF_3)_2CHOCH_2Cl$.

5. A method according to claim 1, wherein the sodium fluoride or potassium fluoride is neither dried nor activated prior to use in the reaction.

6. A method according to claim 3, wherein isoflurane is converted to 2-(difluoromethoxy)-1,1,1,2-tetrafluoroethane.

7. A method according to claim 4, wherein said compound is converted to sevoflurane.

8. A method according to claim 1, wherein the temperature is in the range of 100° to 300° C.

9. A method according to claim 8, wherein the temperature is in the range of 150° to 250° C.

10. A method according to claim 1, wherein the pressure is in the range of 15 to 1100 psig.

11. A method according to claim 10, wherein the pressure is in the range 40 to 600 psig.

12. A method according to claim 1, wherein the molar ratio of said sodium fluoride or potassium fluoride to said compound is about 1:1.

* * * * *